US009850461B2

(12) United States Patent
Rizzi et al.

(10) Patent No.: US 9,850,461 B2
(45) Date of Patent: Dec. 26, 2017

(54) HYDROGEL PRECURSOR FORMULATION AND PRODUCTION PROCESS THEREOF

(71) Applicant: QGEL SA, Lausanne (CH)

(72) Inventors: Simone Rizzi, Novazzano (CH); Matthias Lutolf, Tolochenaz (CH)

(73) Assignee: QGEL SA, Lausanne (CH)

( * ) Notice: Subject to any disclaimer, the term of this patent is extended or adjusted under 35 U.S.C. 154(b) by 60 days.

(21) Appl. No.: 14/684,490

(22) Filed: Apr. 13, 2015

(65) Prior Publication Data

US 2015/0247119 A1   Sep. 3, 2015

Related U.S. Application Data

(62) Division of application No. 13/640,141, filed as application No. PCT/EP2011/056187 on Apr. 19, 2011, now abandoned.

(30) Foreign Application Priority Data

Apr. 22, 2010   (EP) ..................................... 10160796

(51) Int. Cl.
*C12N 5/00* (2006.01)
*C08G 65/334* (2006.01)
*C08G 75/04* (2016.01)

(52) U.S. Cl.
CPC ....... *C12N 5/0068* (2013.01); *C08G 65/3344* (2013.01); *C08G 75/04* (2013.01); *C12N 2533/30* (2013.01); *C12N 2533/50* (2013.01)

(58) Field of Classification Search
None
See application file for complete search history.

(56) References Cited

U.S. PATENT DOCUMENTS

| | | | |
|---|---|---|---|
| 6,495,127 B1 | 12/2002 | Wallace et al. | |
| 6,703,047 B2 | 3/2004 | Sawhney et al. | |
| 2005/0065281 A1 | 3/2005 | Lutolf et al. | |
| 2006/0147395 A1 | 7/2006 | Lyngstadaas et al. | |
| 2008/0187568 A1 | 8/2008 | Sawhney | |
| 2008/0187591 A1* | 8/2008 | Rhee .................... | A61L 24/001 424/484 |
| 2009/0042825 A1 | 2/2009 | Matar et al. | |
| 2009/0098083 A1* | 4/2009 | Hubbell ........... | A61K 47/48215 424/78.27 |
| 2009/0324720 A1 | 12/2009 | He et al. | |

FOREIGN PATENT DOCUMENTS

| | | |
|---|---|---|
| JP | 2000515130 A | 11/2000 |
| JP | 2003505471 A | 2/2003 |
| JP | 2003508564 A | 3/2003 |
| JP | 2005329264 A | 12/2005 |
| WO | 00/44808 A1 | 8/2000 |
| WO | 0044808 | 8/2000 |
| WO | 2006067221 A2 | 6/2006 |
| WO | 2008097581 A1 | 8/2008 |
| WO | 2009021017 A2 | 2/2009 |

OTHER PUBLICATIONS

Sugahara, M.P. et al. 2010.Coadministration of a Tumor-Penetrating Peptide Enhances the Efficacy of Cancer Drugs. Science 328: 1031-1035. Published online Apr. 8, 2010. specif. p. 1032, 1035.
Lutolf, M.P. et al. 2003. Synthesis and Physicochemical Characterization of End-Linked Poly (ethylene glycol)-co-peptide Hydrogels Formed by Michael-Type Addition. Biomacromolecules 4:713-722. specif. pp. 713-714.
Monahan, F.J. et al., Effect of pH and temperature on protein unfolding and thiol/disulfide interchange reactions during heat-induced gelation of whey proteins. Journal of Food Chemistry (1995) 43:46-52; pp. 46, 47, 49.
Dictionary of Chemical Engineering. Caking.Oxford University Press (publisher). First edition. Copyright 2014 Oxford University Press. Ed: Carl Schaschke. Editorial Offices, Oxford, UK. p. 49.
Japanese Office Action issued in the corresponding Japanese Patent Application No. 2015-219514 dated Aug. 23, 2016.
Friedman et al., "Application of a Hammett-Taft Relation to Kinetics of Alkylation of Amino Acid and Peptide Model Compounds with Acrylonitrile", Acrylonitrile Alkylation of Amino Acids, vol. 86, pp. 3735-3741, Sep. 20, 1964.
Friedman et al., "Relative Nucleophilic Reactivities of Amino Groups and Mercaptide Ions in Addition Reactions with α,β-Unsaturated Compounds", Journal of the American Chemical Society, 87:16, pp. 3740-3741, Aug. 20, 1965.
Lutolf et al., "Systematic Modulation of Michael-Type Reactivity of Thiols through the Use of Charged Amino Acids", Bioconjugate Chem. 2001, 12, pp. 1051-1056, Sep. 21, 2001.
Lutolf et al., "Synthesis and Physicochemical Characterization of end-Linked Poly(ethylene glycol)-co-peptide Hydrogels Formed by Michael-Type Addition", Biomacromolecules 2003, 4, pp. 713-722, Feb. 26, 2003.
Grimsley et al., "A summary of the measured pK values of the ionizable groups in folded proteins", Protein Science 2009, vol. 18, pp. 247-251, Dec. 2, 2008.

* cited by examiner

*Primary Examiner* — Renee Claytor
*Assistant Examiner* — Sharon M Papciak
(74) *Attorney, Agent, or Firm* — Davis & Bujold, PLLC; Michael J. Bujold

(57) ABSTRACT

The present invention relates to a hydrogel precursor formulation, its process of production as well as a kit comprising said formulation and a method of production of a hydrogel using said formulation. The precursor formulation comprises at least one structural compound, preferably vinyl sulfone (acrylated branched) poly(ethylene glycol), and at least one linker compound, preferably a peptide with two cysteines, wherein said structural compound and said linker compound are polymerizable by a selective reaction between a nucleophile and a conjugated unsaturated bond or group. The precursor formulation is in the form of a powder.

16 Claims, 2 Drawing Sheets

HYDROGEL PRECURSOR FORMULATION AND PRODUCTION PROCESS THEREOF

Figure 1:
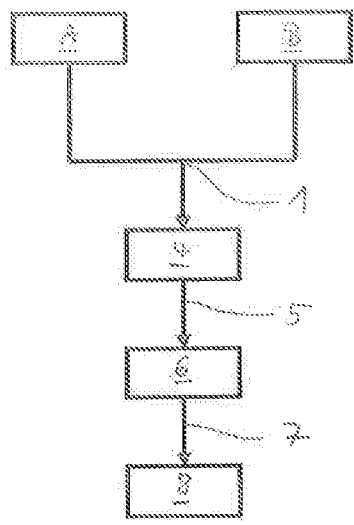

The present invention relates to a hydrogel precursor formulation, its process of production as well as a kit comprising said formulation and a method of production of a hydrogel using said formulation.

Three dimensional cell culture scaffolds have been recognized to allow patterns of gene expression and other cellular activities that more closely mimic living organisms than the conventional two dimensional cell cultures in dishes.

This has led to the development of novel families of synthetic polymer hydrogels, which are often termed artificial ECMs (aECM), since they mimic many aspects of the extracellular matrix. One major challenge is to provide a chemistry which allows cross-linking of the matrix in the presence of cells or bio-molecules as well as stable tethering of biomolecules to the matrix itself.

In recent years, different mechanisms were developed allowing the formation of gels in the presence of cells or biomolecules. For example, mechanisms based on the self-assembly of low molecular weight building blocks such as peptides (Estroff et al,: Water gelation by small organic molecules; Chem. Rev. 2004; 104(3); 1201-18) or ueidopy-rmimidinone (Zhang S.: Fabrication of novel, biomaterials through molecular self-assembly; Nat. Biotechnol. 2003; 21(10); 1171-8) and moderate molecular weight amphiphilic block copolymers (e.g. see Hartgerink et al.: Peptide-amphiphile nanofibers: A versatile scaffold for the preparation of self-assembling materials; Proc. Nat. Acad. Sci. U.S.A. 2002; 99(8); 5133-8) were proposed.

WO 00/44808 describes novel biomaterials, especially for the formation of hydrogels, having a cross-linking chemistry based on a Michael-type addition reaction between a nucleophile and a conjugated unsaturated bond or group, which allows the formation of the gel in the presence of ceils or biomolecules. Moreover, specific signal molecules may be integrated into the gel matrix by a specific reaction.

One major drawback of this system is that it relies on manually mixing at least two precursor components together prior to gelation. In practice, the use of multiple component solutions may be a source of error due to unintentional variations of i) the re-suspension conditions of the different components in powder form, ii) the mixing ratios of the precursor solutions, thus leading to more complex use and reproducibility problems of the gel compositions. Additionally, the upscale of a manufacturing process of a gel system that requires the mixing of several solutions is more expensive than the upscale of a manufacturing process of a gel requiring a single.

It is therefore an objective of the present invention to avoid the disadvantages of the known hydrogel formulations and specifically to provide a hydrogel precursor formulation which is easy in handling and which enables the production of hydrogels with highly reproducible compositions. This objective is solved with a hydrogel precursor according to claim 1.

The hydrogel precursor formulation according to the present invention comprises at least one structural compound and at least one linker compound. The structural and the linker compound are polymerizable by a selective reaction between a nucleophile and a conjugated unsaturated bond or group. The hydrogel precursor formulation is in the form of an unreacted powder.

The formulation has the advantage that the powder may simply be re-suspended, preferably in a buffer, to start the gelling reaction. No mixing of different components is required, thus considerably reducing the probability of erroneous ratios between the at least one structural compound and the at least one linker compound. Thus, this increases the reproducibility of the hydrogels produced from these hydrogel precursors. Moreover, the hydrogel precursor of the present invention provides ease of use.

The hydrogel precursor formulation of the present invention is in the form of a powder. The powder may comprise particles having any size and shape. Alternatively, the powder may also be provided as pressed tablet or pill. Host preferably, the powder is provided in the form of a stable compact cake, e.g. at the bottom of a container.

The powder is unreacted, meaning that almost none of the at least, one structural compound has reacted with the at least one linker compound via the selective reaction. Preferably more than 70%, more preferably more than 85%, most preferably more than 95% of the compounds have not undergone the selective reaction.

The selective reaction is a reaction between a nucleophile and a conjugated unsaturated bond or group by nucleophilic addition. Such reactions are also known as Michael-Type addition reactions.

The structural compound has a functionality of at least three, but most preferably the structural compound has a functionality of four or more. By "functionality" the number of reactive sites on a molecule is meant.

The structural compound is preferably selected from the group consisting of oligomers, polymers, biosynthetic or natural proteins or peptides end polysaccharides. Preferably, the structural compound is a polymer selected from the group consisting of poly(ethylene glycol), poly(ethylene oxide), poly(vinyl alcohol), poly(ethylene-co-vinyl alcohol), poly(acrylic acid), poly (ethylene-co-acrylic acid), poly(ethyloxazoline), poly(vinyl pyrrolidone), poly(ethylene-co-vinyl pyrrolidone), poly(maleic acid), poly(ethylene-co-maleic acid), poly(acrylamide), or poly(ethylene oxide)-co-poly(propylene oxide) block copolymers or mixtures thereof. More preferably, the structural compound is a poly(ethylene glycol), most preferably a branched poly (ethylene glycol) with three, four or more arms.

The linker compound has a functionality of at least two and is selected from the group consisting of oligomers, polymers, biosynthetic or natural proteins or peptides and polysaccharides or mixtures thereof. Preferably, the linker compound is a peptide sequence, most preferably containing an adhesion site, a growth factor binding site, or as protease binding site.

The nucleophile preferably is a strong nucleophile, such as a thiol or a thiol containing group. The nucleophile could also he any other type of nucleophile known in the art, provided that it is strong enough to undergo the selective reaction, e.g. such as an amine. Further, the conjugated unsaturated group preferably is an acrylate, an acrylamide, a quinone or a vinylpyridinium. Most preferably, the unsaturated group is a vinyl sulfone.

Additionally, the hydrogel precursor formulation of the present invention may comprise at least, one bioactive compound, preferably comprising an RGD peptide sequence, which is conjugatable with the structural compound through a selective reaction between a nucleophile and a conjugated unsaturated bond or group.

The bioactive compound may comprise an adhesion site, such as the RGD sequence from fibronectin or the YISG sequence from laminin; a growth factor binding site, such as a heparin binding site; a protease binding site or a therapeutically active compound. Preferably, the bioactive compound comprises a cell adhesion site, most preferably an RGD sequence.

The bioactive compound comprises at least one active group capable of undergoing the self selective reaction. More preferably, the bioactive compound comprises at least one nucleophilic group, most preferably a thiol group.

The bioactive compound is conjugateable with the structural compound through a sell selective reaction between a nucleophile and a conjugated unsaturated bond or group. Most preferably, this self selective reaction is the same reaction as the self selective reaction between the structural compound and the linker compound, especially between the same type of nucleophile and conjugated unsaturated bond or group. Alternatively, the bioactive compound many be conjugated to the structural compound through a self selective reaction prior to the polymerization of the linker compound with the structural compound.

The structural compound preferably is a multi-branched poly (ethylene glycol) (PEG) with functionalized end groups. More preferably, the end groups are functionalized with vinyl sulfone. Most preferably, the structural compound is PEG-tri(vinyl sulfone) or PEG-tetra (vinyl sulfone). Vinyl sulfone functionalization of the alcohol groups off PEG may be carried out with any suitable reaction known in the art. By using branched PEG with three, four or more arms it is possible to produce structural compounds with a functionality of three, four or more.

Preferably, the linker comprises at least two nucleophilic groups, preferably thiol groups. Thiols are strong nucleophiles readily undergoing Michael-Type addition reactions with unsaturated bonds or groups at physiological pH. Moreover, thiols are commonly found in biological systems, so that their use poses no issue in view of toxicity.

The linker compound preferably is a peptide comprising at least two cysteins, preferably located, near the N- and C-terminus of the peptide. Synthesizing peptides with two or more cysteine residues is straightforward. It is further possible to introduce specific protease sites in the peptide such as to produce degradable hydrogels, e.g. for in-vivo use. Further, by varying the amino acids neighbouring the cysteines, it is possible to change the pKa value of the thiol group.

Preferably, the cysteins are located at the N- and C-terminus of the peptide, resulting in peptides with the structure if $H_2N$ CXXXXXXXXC-COOH (SEQ ID NO: 1), preferably with an acetylated N-terminus, Ac; and an amidated C-terminus, NH2; where C is the one letter representation of cysteine and X represents any amino acid except cysteine. The peptide may be of any length, than the number of X ($X_n$) may be any number. Preferably, the peptide has a length of 16 amino acids. Alternatively, the cysteins might be located one or more amino acids away from, the N- or C-terminus, e.g. resulting in peptides with the general structure $H_2N$-$X_m$C$X_n$C$X_p$-COOH (SEQ ID NO: 2), where m, n and p may be any integer, including zero.

Most preferably, the linker compound is a peptide with the sequence $NH_2$-GCRE-XXXXXXXX-ERCG-COOH (SEQ ID NO: 3). The Glycine (G) serves as spacer, the Arginin (R) increases the reactivity of the thiol group of the neighbouring cysteine, and the glutamic acid (E) enhances the solubility of the peptide in aqueous solutions.

Most preferably, the sequence of the linker compound is $NH_2$-GCRE-GPQGIWGQERCG-COOH [SEQ ID NO: 4] or $NH_2$-GCREGDQGIAGFERCG-COOH [SEQ ID NO: 5], again preferably with an acetylated N-terminus and an amidated C-terminus.

Peptides for the linker and Proactive compounds should be synthesized and processed in acidic solvents, most preferably in solutions containing trifluoroacetate (TFA). Residual TFA bound to the peptide powder after peptide synthesis has the effect to lower the pH of a water suspension containing the respective peptide below 4.

The structural compound and/or the linker compound are selected such that the reaction rate of the selective reaction between the structural compound and the linker compound is hindered or highly reduced in the mixing conditions. Preferably, the reaction rate is highly reduced at or below pH 4 compared to at or above pH 7.

A selection of the compounds in this way allows to provide a precursor formulation which will readily undergo gelation reaction at physiological conditions, but which allows its preparation under conditions such that no or almost no selective reaction occurs.

Preferably, the structural and/or the linker compound are selected such that the reaction rate of the self selective reaction is at least twice as fast at pH 7.5 compared to pH 7.0.

Another objective of the present, invention is to provide a production process for a hydrogel precursor formulation. This problem is solved by a process as claimed in claim 8.

The process comprises the steps of:
providing a first solution A comprising at least one structural compound;
providing a second solution B comprising at least one linker compound;
mixing of the solutions A and B; and
lyophilization of the resulting precursor solution The at least one structural compound and the at least one linker compound are polymerizable by a selective reaction between a nucleophile and a conjugated unsaturated bond or group. Both solutions A and B are mixed under conditions which hinder the selective reaction.

This process allows the production of a hydrogel precursor formulation in form of a powder comprising both the structural compound as well as the linker compound. The mixing conditions have to be selected in such a way, that the self selective reaction is hindered. This means that the reaction rate is sufficiently low, that a very large fraction of the compounds of both solutions A and B do not react through the self selective reaction prior to lyophilization. Preferably, more than 70%, more preferably more than 85%, most preferably more than 90% of the molecules in both solutions have not undergone the selective reaction prior to the lyophilization step.

The mixing conditions may be selected by adjustment of pH, concentration of the different compounds, process time, temperature or solvent condition. Most preferably, the mixing is carried out at or below pH 4. Especially when a thiol is used as nucleophile, a pH at or below 4 sufficiently hinders the self selective reaction. Mixing is preferably performed at room temperature.

It is important that solution A is added to solution B, since the pH of solution A is around 7, whereas the pH of solution B is below 4. If solution B was added to solution A, the self selective polymerization reaction would start during the mixing step. When adding solution A to solution B, the pH of the resulting solution will always be below pH 4, therefore hindering the reaction.

Solution A preferably comprises 5-10% w/v of the at least one structural compound. Most preferably, solution A comprises 7.5% w/v of the at least one structural compound.

Further, solution B preferably comprises 0.1-2% w/v of the at least one linker compound. Most preferably, solution B comprises 1% w/v of the at least one linker compound. This concentration of the linker compound provides for good solubility of the compound in the solution.

Using the concentrations of the structural and the linker compounds as mentioned above for both solutions A and B leads to the formation of a compact powder after the lyophilisation step. This compact powder will form a cake-like layer on the bottom of a container, which is favourable. Additionally, using these relatively low concentrations of both compounds during the production process additionally reduces the probability of unwanted pre-mature reactions between the structural and the linker compound. Further, material losses in subsequent production steps are reduced with these concentrations compared with higher concentrations.

Further, solution A and/or solution B preferably are solutions of the at least one structural compound or the at least one linker compound, respectively, in distilled water. Thus, both compounds are present in an un-buffered solution. Due to the trifluoro acetic acid adhering to the peptide linker compound of solution B, the pH of this solution will be reduced. This leads to a pH which is preferably under 4 for the resulting mixture of solutions A and B. More preferably, the pH of the resulting solution is around 3.5.

Alternatively, prior to mixing with solution B, solution A) may be mixed with an additional solution C comprising a biologically active compound which is dimerizable with the structural compound by a selective reaction between a nucleophile and a conjugated unsaturated bond or group. This bioactive compound may comprise an adhesion site, such as the RGD sequence from fibronectin or the YISG sequence from laminin; a growth factor binding site, such as a heparin binding site; a protease binding site or a therapeutically active compound. Preferably, the bio-active compound comprises a cell adhesion site, most preferably an RGD sequence.

Preferably, solution C comprises 0.1 to 10% w/v of the biologically active compound. More preferably, solution C comprises between 0.1 and 5%, most preferably between 0.1 and 2% of the biologically active compound.

Variation of the respective amounts of the structural, compound in solution A and the biologically active compound in the optional solution C as well as the concentration and nature (e.g. amino acid sequence) of the linker compound in solution B allows the production of hydrogel precursor formulations with different characteristics.

Although the possibilities of variation of the concentration of the compounds in each of solution A and B are many, it is preferred that the concentration of the compounds is selected such that the molar ratio of the nucleophile to the conjugated unsaturated bond or group results in optimal physicochemical properties, like maximum shear modulus and minimal swelling characteristics of the final gels. Normally the optimal ratio of the nucleophile to the conjugated unsaturated bond or group is within the range of 0.8:1 to 1.3:1. This ensures the formation of a hydrogel where almost all active groups have undergone the selective reaction, so that side reactions of any of the reactive groups are considerably reduced.

Further the precursor solution may be subjected to filtration prior to the lyophilization steps. The filtration preferably is a sterile filtration. Any undissolved compounds as well as bacterial contaminations may be removed from the mixture prior to the lyophilization step.

Preferably, the pre-mixed precursor solution is aliquoted and filled into containers, preferably sterile containers, before the lyophilization step. This allows the production of single containers containing a defined amount of a hydrogel precursor formulation. The containers may be of any suitable material, such as plastic or glass. Preferably the containers are vials.

The containers are preferably filled with sterile nitrogen gas and capped immediately after the lyophilization step. This protects the hydrogel precursor powder from contact with moisture and/or oxygen, which may lead to premature polymerization or oxidation of the nucleophiles.

Another object of the present invention is the use of a hydrogel precursor formulation as described herein for the manufacture of a hydrogel.

A further object of the present invention is to provide a simple so use system for the production of hydrogels with highly reproducible results.

The kit of the present invention comprises at least, one container filled with a hydrogel precursor formulation as described herein and a container with a reaction buffer. The container contains preferably an amount of precursor formulation powder, which will result in a gel with predefined characteristics when re-suspended with a defined amount of reaction buffer.

The reaction buffer preferably has a pH above 7. More preferably the reaction buffer has a pH between 7 and 8. The buffer preferably comprises HEPES, preferably ads 0.3 M concentration with the pH adjusted to a value between 7 and 8. This allows for a sufficiently fast polymerization reaction.

A further object of the present invention is to provide an easy to use method to produce a hydrogel.

The method of production of a hydrogel comprises the steps of:
  Re-suspending a hydrogel precursor formulation as described herein in a buffer having pH 7, more preferably with a buffer having a pH between 7 and 8;
  Optionally adding a cell culture suspension to the precursor suspension;
  Casting of a gel precursor with the precursor suspension; and
  Polymerization of the gel precursor for at least 30 minutes, preferably for 30 to 45 minutes, preferably in an incubator at 37° C.

The hydrogel precursor formulation of the present invention is polymerisable under physiological conditions, which allows the addition of a cell culture to the precursor suspension so that the cells may be evenly distributed in the suspension prior to gelation. This would not readily be possible with any other precursor system.

Further details and benefits of the present invention will be apparent from the following figures and examples:

FIG. 1: Schematic representation of an embodiment of a manufacturing process of as hydrogel precursor formulation according to the present invention FIG. 2: Schematic representation of a second embodiment of a manufacturing process of a hydrogel precursor formulation according to the present invention FIG. 3: Schematic representation of a third embodiment of a manufacturing process of a hydrogel precursor formulation according to the present invention FIG. 1 shows a schematic representation of an embodiment of a manufacturing process of a hydrogel precursor formulation according to the present invention. Solution A comprising 7.5% w/v of branched PEG with 4 arms functionalized with vinyl sulfone is added to solution B comprising 1% w/v of a peptide sequence with two cysteines, one near the C- and the other near the N-terminus, in mixing step 1.

For example, 275 mL of solution A. comprising 7.5% w/v of functionalized PEG is added to 425 mL of solution B comprising 1% w/v of a linker peptide.

Solutions A and B are prepared by suspending the respective compounds in distilled water. For solution B, the peptide linker compound is preferably added to the water in small portions. Mixing is carried out under continuous stirring with a magnetic stirrer at 400 PPM. The so obtained precursor solution 4 is subsequently subjected to a sterile filtration step 5, e.g. using a Mini Kleenpak filter (PALL Corp.) with a PTFE membrane with an absolute rating of 0.2 μm, yielding the filtrated precursor solution 6. This solution is then subjected to lyophilization step 7, resulting in the hydrogel precursor formulation 8 in form of a powder. The resulting powder is in the form of a stable compact cake.

Lyophylization step 7 may be carried out by first freezing the solution a shelf at −50° C. for 150 min, followed by a first drying step at −10° C. for 570 min at a pressure of 0.26 mbar. A second drying step follows at a temperature of 20° C. for 180 min at a pressure of 0.02 mbar.

Figure 2:
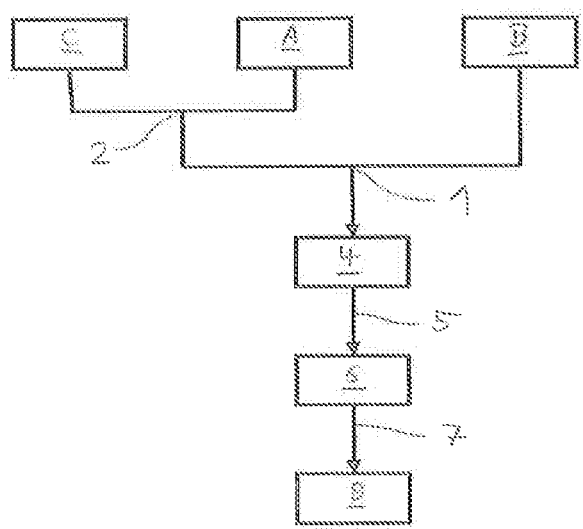

On FIG. 2 a second embodiment of a manufacturing process of a hydrogel precursor formulation according to the present invention is schematically represented. In this embodiment Solution A comprising 7.5% w/v of a branched PEG with 4 arms functionalized with vinyl sulfone is mixed with Solution C comprising 2% w/v of a peptide comprising an RGD sequence m mixing step 2.

For example, 275 mL of Solution A comprising 7.5% w/v of a functionalized four branched PEG is mixed with 5 mL of Solution C comprising 2% w/v of a bioactive compound. This solution is then subsequently mixed with solution B comprising 1% w/v of a peptide linker comprising two systems, one near the C- and the other near the N-terminus, in mixing step 1.

The so obtained precursor solution 4 is subsequently subjected, to a sterile filtration step 5, yielding the filtrated precursor solution 6. This solution is then subjected to lyophilization step 7, resulting in the hydrogel precursor formulation 8 in form of a powder.

Figure 3:
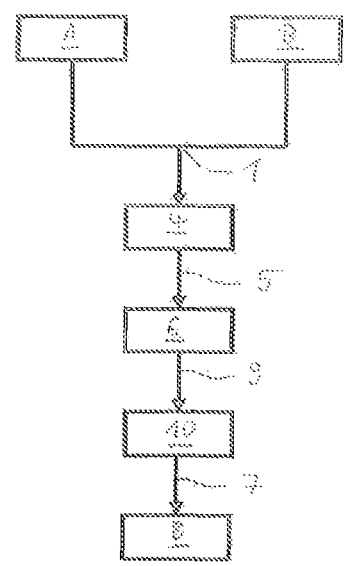

FIG. 3 shows a third embodiment of a manufacturing process of a hydrogel precursor formulation according to the present invention. Solution A comprising 7.5% w/v of branched PEG with 4 arms functionalized with vinyl sulfone is mixed with Solution B comprising 1% w/v of a linker peptide sequence with a cysteine near the C- and N-terminus, in mixing step 1. Solutions A and B are prepared by suspending the respective compounds in distilled water. The mixing is carried cut under continuous stirring with a magnetic stirrer, preferably at 400 RPM. The so obtained precursor solution 4 is subsequently subjected to a sterile filtration step 5, yielding the filtrated precursor solution 6. This solution is often aliquoted into containers in aliqoting step 9. Each container may contain only a small amount, preferably 0.3-0.4 mL. The containers are scalable and are preferably made of glass. The aliquoted precursor solution 10 is the lyophilized in lyophilization step 7 to yield the precursor formulation powder 8.

The invention claimed is:

1. A process for the production of a hydrogel precursor formulation in the form of a powder comprising the steps of:
   providing a first solution A of at least one structural compound, wherein the structural compound is a multi-branched polyethylene glycol (PEG) functionalized with vinyl sulfone;
   providing a second solution B comprising at least one linker compound, wherein the linker compound is a peptide comprising at least two cysteines;
   mixing of the solutions A and B, which results in a precursor solution;
   filling the precursor solution into at least one container; and
   lyophilization of the resulting precursor solution,
   wherein a compact powder, which is in the form of a stable cake at the bottom of the at least one container, results from the lyophilization, and wherein the structural compound, and the linker compound are polymerizable by a selective reaction between a nucleophile and a conjugated unsaturated bond or group, and the solutions A and B are mixed under conditions which hinder the selective reaction.

2. The process as claimed in claim 1, wherein the solutions A and B are mixed at or below pH 4.0.

3. The process as claimed in claim 1, wherein solution A comprises 5-10% w/v of the at least one structural compound.

4. The process as claimed in claim 1, wherein solution B comprises 0.1-2% w/v of the at least one linker compound.

5. The process as claimed in claim 1, wherein a solution C comprising at least one biologically active compound which is dimerizable with the structural compound by the selective reaction between the nucleophile and the conjugated unsaturated bond or group is added to the solution A prior to the mixing of the solutions A and B.

6. The process as claimed in claim 5, wherein solution the C comprises 0.1-10% w/v of the at least one active compound.

7. The process as claimed in claim 5, wherein the at least one structural compound, the at least one linker compound, and the at least one biologically active compound are a solution of the at least one structural compound, the at least one linker compound and the at least one biologically active compound, respectively, in distilled water.

8. The process as claimed in claim 1, wherein the concentration of the at least one structural, and the at least one linker compounds is selected such that a molar ratio of the nucleophile to the conjugated unsaturated bond or group is in a range of 0.8:1 to 1.3:1.

9. The process as claimed in claim 1, wherein the precursor solution is subjected to filtration prior to the lyophilization step.

10. The process as claimed in claim 1, wherein the precursor solution is aliquoted and filled into containers before the lyophilization step.

11. The process as claimed in claim 10, wherein the containers are filled with sterile nitrogen gas and capped immediately after the lyophilization step.

12. A kit of parts comprising at least one container filled with a hydrogel precursor formulation comprising at least one structural compound and at least one linker compound,
   wherein said structural compound and said linker compound are polymerizable by a selective reaction between a nucleophile and a conjugated unsaturated bond or group,
   the hydrogel precursor formulation is in the form of an unreacted powder,
   said unreacted powder is in the form of a stable compact cake, and
   a container with a reaction buffer.

13. The kit of parts as claimed in claim 12, wherein the reaction buffer has a pH of at least 7.

14. A method of production of a hydrogel comprising the steps of:
   providing the hydrogel precursor formulation of claim 1 comprising the at least one structural compound and the at least one linker compound in the container, wherein said structural compound and said linker compound are polymerizable by a selective reaction between a nucleophile and a conjugated unsaturated bond or group, wherein the hydrogel precursor formulation is in the form of an unreacted powder, and wherein said unreacted powder is in the form of a stable compact cake,
   resuspending the hydrogel precursor formulation in a buffer having a pH of between 7 and 8;
   casting a gel precursor with the hydrogel precursor formulation resuspension; and
   allowing polymerization of the gel precursor for at least 30 minutes, to form a hydrogel.

15. The method of production of a hydrogel as claimed in claim 14 comprising the step of adding a cell culture suspension to the precursor suspension.

16. The method of production of a hydrogel as claimed in claim 14, comprising the step of performing polymerization in an incubator at 37° C.

* * * * *

SEQUENCE LISTING

```
<160> NUMBER OF SEQ ID NOS: 5

<210> SEQ ID NO 1
<211> LENGTH: 302
<212> TYPE: PRT
<213> ORGANISM: Artificial Sequence
<220> FEATURE:
<223> OTHER INFORMATION: Designed peptide used as linker compound
<220> FEATURE:
<221> NAME/KEY: VARIANT
<222> LOCATION: (2)..(301)
<223> OTHER INFORMATION: Xaa = any amino acid; any one or all of amino
      acids 2-301 can either be present or absent

<400> SEQUENCE: 1

Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
```

```
                130                 135                 140
Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
                180                 185                 190

Xaa Xaa Xaa Xaa Xaa Xaa Xaa Xaa Xaa Xaa Xaa Xaa Xaa Xaa Xaa
            195                 200                 205

Xaa Xaa Xaa Xaa Xaa Xaa Xaa Xaa Xaa Xaa Xaa Xaa Xaa Xaa Xaa
        210                 215                 220

Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa
                260                 265                 270

Xaa Xaa Xaa Xaa Xaa Xaa Xaa Xaa Xaa Xaa Xaa Xaa Xaa Xaa Xaa
            275                 280                 285

Xaa Xaa Xaa Xaa Xaa Xaa Xaa Xaa Xaa Xaa Xaa Xaa Xaa Cys
        290                 295                 300

<210> SEQ ID NO 2
<211> LENGTH: 302
<212> TYPE: PRT
<213> ORGANISM: Artificial Sequence
<220> FEATURE:
<223> OTHER INFORMATION: Designed peptide used as linker compound
<220> FEATURE:
<221> NAME/KEY: VARIANT
<222> LOCATION: (1)..(100)
<223> OTHER INFORMATION: Xaa = any amino acid; any one or all of amino
      acids 1-100 can either be present or absent
<220> FEATURE:
<221> NAME/KEY: VARIANT
<222> LOCATION: (102)..(201)
<223> OTHER INFORMATION: Xaa = any amino acid; any one or all of amino
      acids 102-201 can either be present or absent
<220> FEATURE:
<221> NAME/KEY: VARIANT
<222> LOCATION: (203)..(302)
<223> OTHER INFORMATION: Xaa = any amino acid; any one or all of amino
      acids 203-302 can either be present or absent

<400> SEQUENCE: 2

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Cys Xaa Xaa Xaa Xaa Xaa Xaa Xaa Xaa Xaa Xaa
                100                 105                 110

Xaa Xaa Xaa Xaa Xaa Xaa Xaa Xaa Xaa Xaa Xaa Xaa Xaa Xaa Xaa
```

```
                        115                 120                 125
Xaa Xaa Xaa Xaa Xaa Xaa Xaa Xaa Xaa Xaa Xaa Xaa Xaa Xaa Xaa Xaa
        130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa Cys Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
        210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
        260                 265                 270

Xaa Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa
        290                 295                 300

<210> SEQ ID NO 3
<211> LENGTH: 16
<212> TYPE: PRT
<213> ORGANISM: Artificial Sequence
<220> FEATURE:
<223> OTHER INFORMATION: Designed peptide used as linker compound
<220> FEATURE:
<221> NAME/KEY: VARIANT
<222> LOCATION: (5)..(12)
<223> OTHER INFORMATION: Xaa = any amino acid; any or all of amino acids
      5-12 can either be present or absent

<400> SEQUENCE: 3

Gly Cys Arg Glu Xaa Xaa Xaa Xaa Xaa Xaa Xaa Xaa Glu Arg Cys Gly
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Designed peptide used as linker compound
<220> FEATURE:
<221> NAME/KEY: PEPTIDE
<222> LOCATION: (1)..(16)
<223> OTHER INFORMATION: Designed peptide

<400> SEQUENCE: 4

Gly Cys Arg Glu Gly Pro Gln Gly Ile Trp Gly Gln Glu Arg Cys Gly
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Designed peptide used as linker compound
<220> FEATURE:
<221> NAME/KEY: PEPTIDE
```

-continued

```
<222> LOCATION: (1)..(16)
<223> OTHER INFORMATION: Designed peptide

<400> SEQUENCE: 5

Gly Cys Arg Glu Gly Asp Gln Gly Ile Ala Gly Phe Glu Arg Cys Gly
1               5                   10                  15
```